Figure 1:
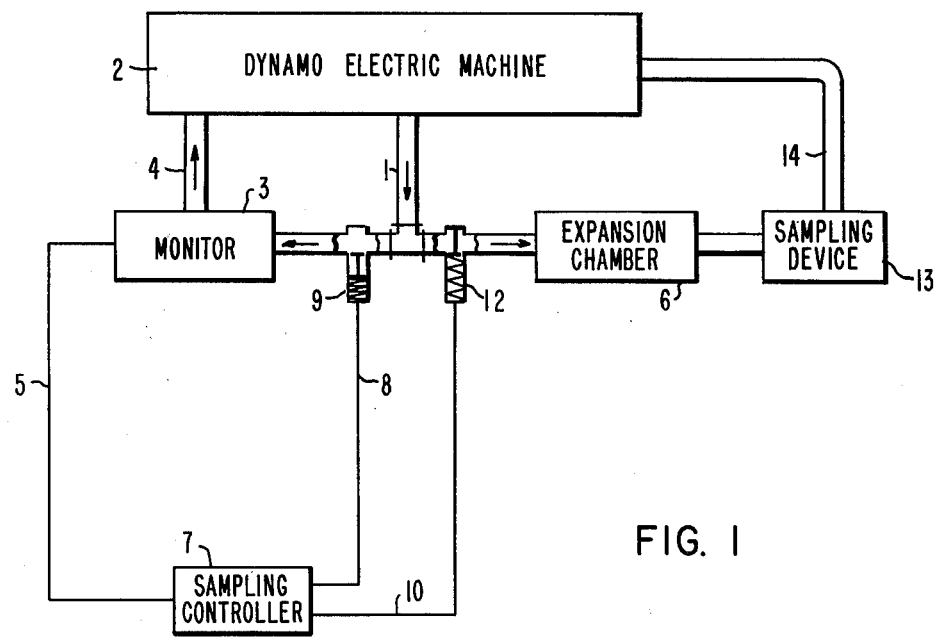

United States Patent [19]

Kaczmarek et al.

[11] 4,135,399

[45] Jan. 23, 1979

[54] USE OF AN EXPANSION CHAMBER FOR THE PRODUCTION OF REPRESENTATIVE PARTICULATE EFFLUENT FROM POLYMERS

[75] Inventors: Thomas D. Kaczmarek, Penn Hills; Richard J. Wengrzyn, Edgewood, both of Pa.

[73] Assignee: Westinghouse Electric Corp., Pittsburgh, Pa.

[21] Appl. No.: 796,576

[22] Filed: May 13, 1977

[51] Int. Cl.² .................. G01K 3/00; G08B 21/00
[52] U.S. Cl. .................................... 73/339 R; 73/28
[58] Field of Search ............ 73/28, 421.5 A, 421.5 R, 73/432 PS

[56] References Cited

U.S. PATENT DOCUMENTS

| 3,007,367 | 11/1961 | Rich | 73/432 PS X |
| 3,427,880 | 2/1969 | Grobel et al. | 73/339 R |
| 3,807,218 | 4/1974 | Carson et al. | 73/28 |
| 3,972,225 | 8/1976 | Fort et al. | 73/28 |

Primary Examiner—Charles A. Ruehl
Attorney, Agent, or Firm—G. H. Telfer

[57] ABSTRACT

A gas stream monitoring system monitors a gas stream of a power generator and causes a sample of the gas stream to be collected if its characteristics indicate that a material in the power generator is being thermally degraded. After verifying that the degradation indication is true, a sample is taken of the gas stream. In order to insure that the sample is representative, an expansion chamber approximately the same size as the ionization chamber of the monitoring device is placed in line prior to the sampling device. The sampling device has three sections which collect large particles, small particulates, and vapors and gases. The products collected can be analyzed to determine which material in the power generator was thermally degraded.

5 Claims, 5 Drawing Figures

USE OF AN EXPANSION CHAMBER FOR THE PRODUCTION OF REPRESENTATIVE PARTICULATE EFFLUENT FROM POLYMERS

BACKGROUND OF THE INVENTION

1. Field of the Invention

This invention relates to gas stream monitoring apparatus and particularly to such apparatus for use with gas cooled dynamoelectric machines.

2. Description of the Prior Art

Large dynamoelectric machines occasionally fail due to thermal degradation of various materials, particularly organic insulation. Since an early detection of the insulation failure is essential to the prevention of a large scale burnout of the dynamoelectric machine, monitoring devices are desirably used which monitor the gas streams that flow through dynamoelectric machines. Presently, most monitors work by detecting particulates in the gas stream, which are found when insulation is being thermally degraded. When the monitor detects degradation products and generates a signal, the flow of the detectable particulates to the monitor is terminated to determine whether the signal is genuine or is due to a malfunction of the monitor. If the signal then terminates it is assumed to be genuine and the generator can be shut down for repair or other precautions taken.

Since down time on a large generator can be costly, it is normally important to locate the insulation failure and repair it quickly. Over 50 different materials are used in generators, including regular and modified expoxies, polyesters, silicones, phenolics, etc., and unless the failure is easily visible, it may be very difficult to locate.

In U.S. Pat. No. 3,972,225, issued Aug. 3, 1976, it was disclosed that if the gas stream is sampled when the monitor indicates that a failure is occurring, the products collected can be analyzed to determine which material in the generator was failing. Since the location of the various material is known, the search for the failure is considerably shortened.

It was also disclosed that the sampling can be done automatically, so that when the monitor produces a signal it can check for authenticity and the sample taken without human interference.

Finally it was disclosed that a particular sampling device, which separates the products of the gas stream into particles 10 microns or greater, particulates less than 10 microns, and vapors and gases, is particularly useful in facilitating the analysis.

SUMMARY OF THE INVENTION

We have found that one of the features of the generator condition monitor used in the prior art is that the ionization chamber containing an alpha source is also a mixing chamber. This chamber is, for example, approximately 7.6 cm in diameter by approximately 25.4 cm long producing a volume of about 1150 cc. This volume is very large in comparison to the pipe feeding it. Thus, it will act as a gas expansion or cooling chamber. In the case where a condensation nuclei type of monitor is used, an expansion chamber is an integral part of its operation.

We have found that by using the prior art system as disclosed in the above-referenced patent and inserting in that system prior to the sampling chamber an expansion chamber, that the resulting cooling and increase in formation residence time aids significantly in the production of aerosol condensates to which the generator condition monitor had responded.

While of particular interest for use with gas (e.g., hydrogen)-cooled electrical apparatus (e.g., generators), it will be apparent the apparatus of this invention may be applied to other gas systems.

BRIEF DESCRIPTION OF THE DRAWINGS

For a better understanding of the invention, references may be had to the preferred embodiments, exemplary of the invention, shown in the accompanying drawings in which:

FIG. 1 is a diagram showing a presently preferred sampling system with an expansion chamber according to this invention;

FIG. 2 is a schematic view of the ionization chamber of the generator condition monitor of FIG. 1;

FIG. 3A is a mass spectra of particulates collected by the prior art method;

FIG. 3B is a mass spectra of particulates collected using the system including an expansion chamber in accordance with this invention.

FIG. 4 is a schematic view of a condensation nuclei dielectric which can be used as an alternate for the detector shown in FIG. 2;

DESCRIPTION OF THE PREFERRED EMBODIMENT

In FIG. 1, conduit 1 carries gas from the gas stream of the dynamoelectric machine 2 to monitor 3 where it is monitored and then returned to the machine through conduit 4.

Monitor 3 checks the gas stream for any characteristics which indicates that thermal degradation of material in the generator is occuring. The thermal degradation may be due to primary failure of the material, or may be a secondary failure which indicates arcing or some other problem is occurring in the generator. Typically, the monitor checks the level of particulates in the gas stream. The operation of the inoization monitor as shown in FIG. 2 is more particulary described in U.S. Pat. No. 3,573,460, issued Apr. 6, 1971. However, if the monitor is the simplified condensation nuclei type of monitor as shown in FIG. 4, then a more detailed description is provided in U.S. Pat. No. 3,427,880, issued Feb. 18, 1969.

Particulates which are small particles or condensed gases, (i.e., liquids, aerosols) less than about 10 microns in size, are formed when organic materials thermally degrade. In fact, some of the materials in the generators may be coated with substances which produce large quantities of particulates at specific low temperatures to aid in the early detection of insulation overheating before failure. Other types of monitors may be used to detect the failure of materials by checking for vapors in the gas stream, pH of the gas stream, optical density or optical absorption of the gas stream, or other characteristics or combination of characteristics.

Referring to FIG. 1, when the monitor detects a failure of a material, it generates a signal, typically an electric signal, which passes through line 5 to sampling controller 7.

Insulation occasionally falls off or is abraded off by friction and some of its dust can be made airborne by the moving parts of the generator. If these dust particles are present in sufficient quantities, they can cause monitor 3 to produce spurious signals for brief periods. These signals do not indicate a genuine material failure due to heat. Sampling controller 7 therefore will block out the flow of gas to the monitor by passing a signal through line 8 and closing valve means 9.

Since stopping a dynamoelectric machine and searching for insulation failure is a very expensive undertaking, monitor 3 must first be checked to determine that it is operating correctly. Depending on the type of monitor used, solenoid valve means 9 therefore terminates the flow of gas to the monitor or diverts the gas through a filter (not shown) which filters out of the gas streams, the particulates or gases that activated the monitor.

If the signal from the monitor then terminates, sampling controller 7 will generate a signal which passes through line 10 to solenoid valve 12 which controls the flow of the gas stream to the expansion chamber 6 and sampling device 13, then to the exhaust system (not shown) through conduit 14.

Figure 2:
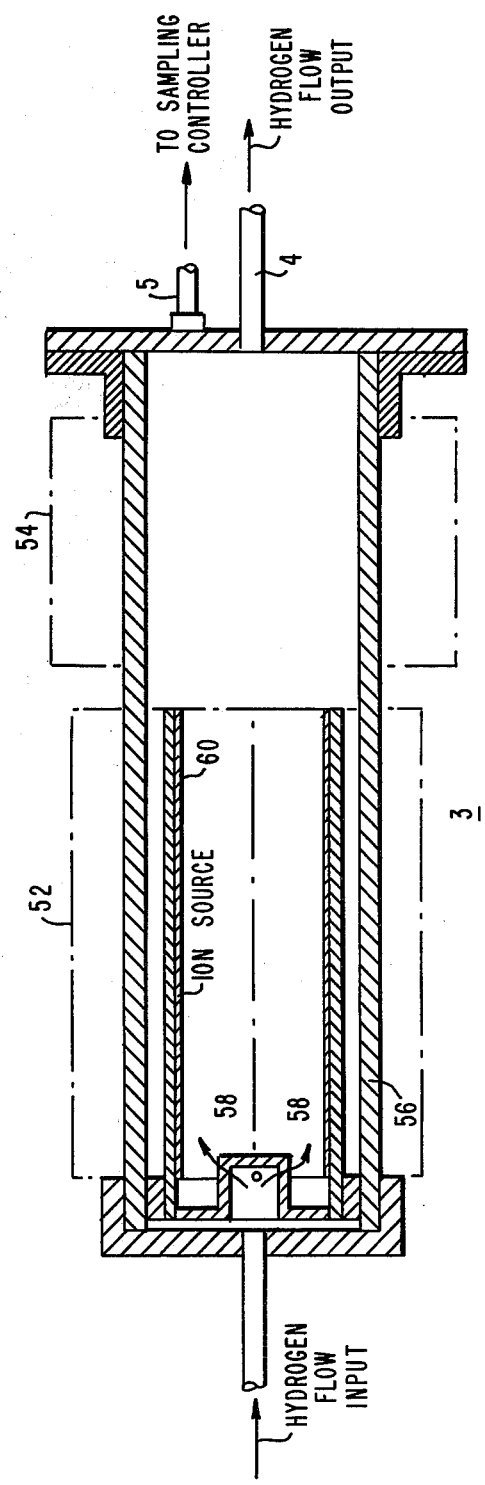

Referring now to FIG. 2, the generator condition monitor 3 preferably comprises an ionization chamber 52 and an ion collection chamber 54 contained in a pressure housing 56. The gas stream flow as represented by arrows 58 passes through the ionization chamber 52 in which a low level radiation source 60 is disposed. The convenient means for ionizing hydrogen gas, which is generally the cooling gas used in dynamoelectric machines comprises a minute amount of thorium 232, which produces 3.999 Mev alphas, and has a half-life of $1.32 \times 10^{10}$ years.

The ionization chamber is approximately 7.6 cm. in diameter by 25.4 cm. long and has a volume of approximately 1150 cc. This volume is very large in comparison to the pipe feeding it. Therefore, it acts as a gas expansion chamber by cooling the gas as it flows into the chamber. This cooling, by increasing the formation residence time, aids in the production of aerosol-type condensates to which the condition monitor responds.

The cooling gas ions produced by the thorium source 60 are carried by the coolant flow into the ion collection chamber 54 which has a pair of collection electrodes (not shown).

Figure 4:
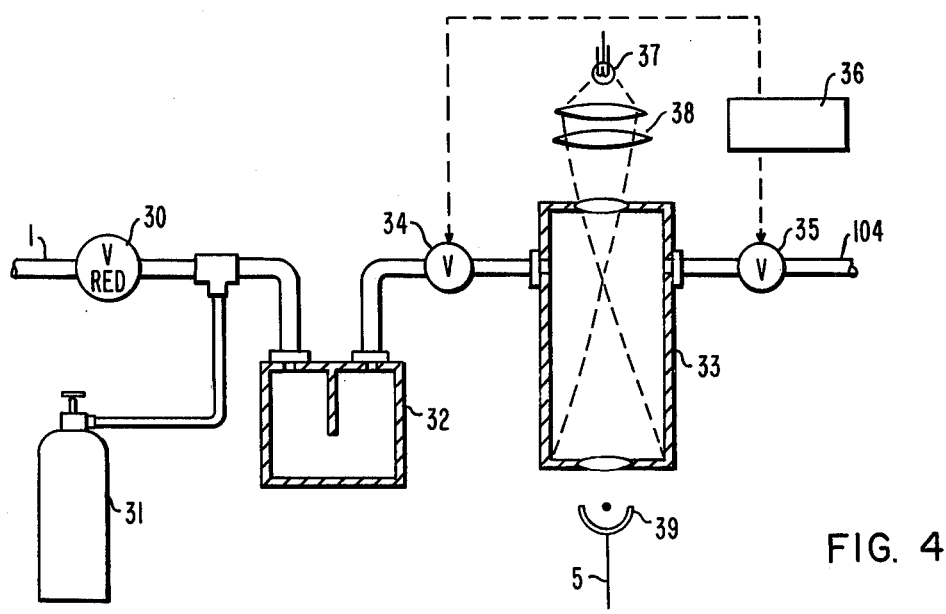

If the gas stream monitor is the simplified condensation nuclei detector shown in FIG. 4, gas from the generator enters the detector through conduit 1 as shown in FIG. 1, is reduced in pressure by reducing valve 30 and diluted with an inert gas, such as nitrogen from bottle 31. The diluted mixture passes through a humidifying chamber 32 which saturates the gas with water vapor. An expansion chamber 33 serves to cyclically expand batches of humidified gas when valves 34 and 35 are alternately opened and closed by an automatic rotary valve actuator 36. A light source 37 and lens system 38 causes the scattered light to be detected by photo tube 39. When the adiabatic expansion occurs, the water vapor condenses on the condensation nuclei (the particulates if present). The scattered light intensity falling on photo tube 39 is related to the number of droplets affected by the presence of particulates. The light responsive signal passes through line 5 to sampling controller 7. In contrast to the system in FIG. 1, the gas after passing through the condensation nuclei detector is preferably discarded through conduit 104 which is connected to an exhaust system (not shown).

Regardless of the type of monitors used, it is felt, in order to collect a more representative sample of the particulate to which the monitor had responded, that the gas, with particulates therein, must be provided with an adequate amount of formation residence time such as that provided by the above discussed detector before being collected by sampling.

Figure 3A:
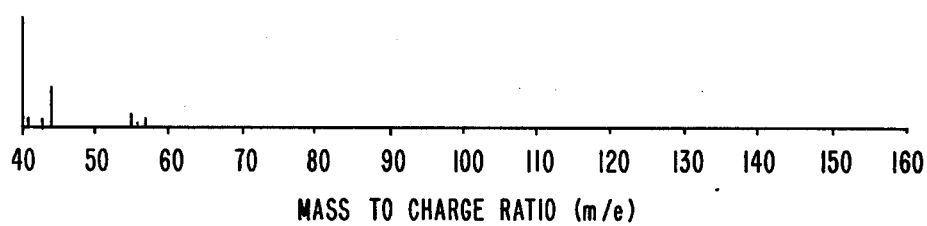

Therefore, we have found by laboratory means that if an expansion chamber was inserted in a gas stream in front of the sampling device, the results of the mass spectra of the collected sample is quite different from the resulting mass spectra of the collected sample without the expansion chamber. In the laboratory experiment a sample of p-Toluenesulfonic acid in SC 193/1 (a modified epoxy coating system) was placed in a tube furnace and hydrogen gas was flowed through the furnace while the furnace was being heated. There was a standard ionization type generator condition monitor in line with the tube furnace and upon an indication that there were thermoparticulates being produced, the generator condition monitor was removed from the line and the flow of hydrogen through the tube furnace was diverted to an effluent trap which collected particulates and vapors. After a sample was collected the mass spectra was ran on the collected samples and the results are shown in FIG. 3A.

Figure 3B:
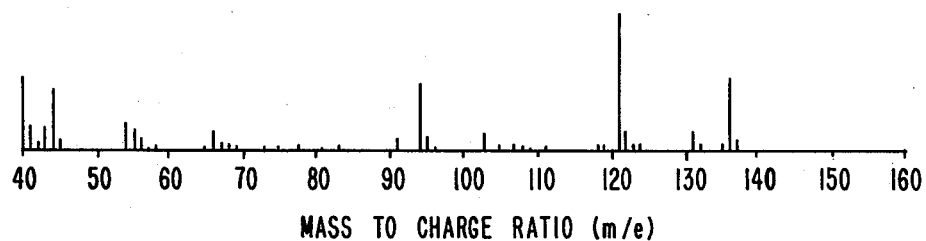

Using the same laboratory setup a generally tubular shaped expansion chamber of 945 cc. was inserted in line between the tube furnace and the effluent trap. Once again, the furnace was heated and as a flow of hydrogen gas passed through it, a second sample was collected. After this sample was collected a mass spectra of the particulates collected in the effluent trap was performed and the results are shown in FIG. 3B. In comparison of the two figures, the mass to charge ratio under the prior art system shows that there were no aerosol condensates or particulates present with a mass to charge ratio greater than 60. However, with the addition of the expansion chamber there are many significant peaks with a mass to charge ratio greater than 60. Amongst these are at 94, at 120 and at 136.

The present particulate traps do not have any antechamber which can act as an expansion and cooling compartment. Furthermore, at a typical gas sampling rate of 5 liters per minute, a particle will have approximately a 14-second formation residence time in a prior art generator condition monitor ionization chamber. By contrast, the standard particulate collector trap has dead space preceeding the particulate collector disc that permits a formation residence time for a particle of only about 0.03 seconds at a sample flow rate of 5 liters per minute.

Therefore, in order to collect a more representative sample of particulates, that the monitor responded to, an expansion chamber should be inserted in line prior to the sampling device that will increase the formation time of the particulates beyond the current prior art system's 0.03 seconds at a flow rate of approximately 5 liters per minute of hydrogen.

We claim:

1. A sampling system comprising:

a gas stream monitoring means for detecting thermal degradation of materials by monitoring the gas stream exposed to the products of said thermal degradation, and for generating a first signal when said thermal degradation is detected;

means for determining whether said gas stream monitoring means is functioning properly when said first signal is generated and if so, for generating a second signal;

a sampling means for sampling said gas stream when said second signal is generated; and a gas expansion means for increased production of aerosol-type condensates disposed between said sampling means and said gas stream.

2. The sampling system according to claim 1 wherein said gas expansion means further comprises a generally tubular shaped chamber disposed in a connecting conduit between said gas stream and said sampling means, said generally tubular shaped chamber having an internal dimension substantially larger than said connecting conduit's internal dimension.

3. In combination a dynamoelectric machine having a gas stream, a gas stream monitor having an ionization chamber and an ion collection chamber, a sampling device for sampling said gas stream and a generally tubular shaped expansion chamber for production of aerosol-type condensates, said expansion chamber connected by inlet conduit means to allow gas stream communication thereto from said monitor, said expansion chamber having a volume large enough to facilitate the cooling of said gas stream thereby producing aerosol condensates, and conduit means to allow communication between said expansion chamber and said sampling device.

4. The combination according to claim 3 wherein said expansion chamber has an internal dimension and a volume equal to said ionization chamber.

5. The combination according to claim 3 wherein said expansion chamber's internal dimensions and volume provide a formation residence time greater than about 0.03 seconds at a flow rate of about 5 liters per minute of said gas stream.

* * * * *